United States Patent [19]

Bonte et al.

[11] Patent Number: 5,676,949
[45] Date of Patent: *Oct. 14, 1997

[54] USE OF A SIMABA EXTRACT TO REDUCE PATCHY SKIN PIGMENTATION, ENHANCE THE PROTECTIVE FUNCTION OF THE SKIN OR PREPARE A SKIN CELL CULTURE MEDIUM AND RESULTING COMPOSITION

[75] Inventors: Frederic Bonte; Alain Meybeck, both of Courbevoie; Marc Dumas, Colombes, all of France

[73] Assignee: LVMH Recherche, Nanterre, France

[*] Notice: The term of this patent shall not extend beyond the expiration date of Pat. No. 5,630,970.

[21] Appl. No.: 448,563

[22] PCT Filed: Dec. 10, 1993

[86] PCT No.: PCT/FR93/01224

§ 371 Date: Aug. 1, 1995

§ 102(e) Date: Aug. 1, 1995

[87] PCT Pub. No.: WO94/13259

PCT Pub. Date: Jun. 23, 1994

[30] Foreign Application Priority Data

Dec. 11, 1992 [FR] France ................................. 92 14969
Aug. 2, 1993 [FR] France ................................. 93 09493

[51] Int. Cl.$^6$ ............................ A61K 35/78; A61K 7/42
[52] U.S. Cl. .................... 424/195.1; 424/59; 424/60; 424/400; 424/401
[58] Field of Search .......................... 424/400, 401, 424/195.1, 59, 60

[56] References Cited

U.S. PATENT DOCUMENTS 4,508,703  4/1985  Redziniak et al. ................. 424/450
4,621,023  11/1986  Redziniak et al. ................. 428/402.2

*Primary Examiner*—Shelley A. Dodson
*Attorney, Agent, or Firm*—Larson and Taylor

[57] ABSTRACT

A simaba extract is used to produce a cosmetic or pharmaceutical, and particularly dermatological, composition or a skin cell culture medium. The resulting compositions are also disclosed. The simaba extract has a significant skin depigmentation activity and can enhance the protective function of the skin, particularly its water barrier function, as well as having a significant keratinocyte differentiation activity.

31 Claims, No Drawings

USE OF A SIMABA EXTRACT TO REDUCE PATCHY SKIN PIGMENTATION, ENHANCE THE PROTECTIVE FUNCTION OF THE SKIN OR PREPARE A SKIN CELL CULTURE MEDIUM AND RESULTING COMPOSITION

The present invention relates essentially to the use of a simaba extract for the manufacture of a cosmetic or pharmaceutical composition, especially dermatological composition, which has especially a depigmentation activity and an activity promoting keratinocyte differentiation, and which is intended in particular for reducing patchy skin pigmentation, especially liver spots, treating vitiligo, enhancing the protective function of the skin or improving the appearance of the hair, or for the preparation of a skin cell culture medium, and to the composition thus obtained.

More particularly, the invention relates to the use of a simaba extract for the manufacture of a cosmetic or pharmaceutical composition, especially dermatological composition, which has especially a depigmentation activity as well as an activity promoting keratinocyte differentiation, and which is intended in particular for treating patchy skin pigmentation, especially liver spots, treating vitiligo and skin disorders accompanied by keratinocyte differentiation disorders, such as psoriasis, restoring, preserving and/or enhancing the protective function of the skin, especially the water barrier function, and the cohesion of the epidermal cells, or else improving the quality of the hair, or for the preparation of a cell or tissue culture medium, especially for the mass culture of skin cells, in particular keratinocytes.

The simaba plant is a plant belonging to the Simaroubaceae family. Among the simaba plants, there may be mentioned *Simaba cedron* (Planchon), *Simaba cuspidata* (Spruce), *Simaba moretii*, *Simaba multiflora* (Adr. Juss.) and *Simaba guyanensis* (Aublet Engl.).

These plants are known to have similar properties (see the following books: "Pharmacopées traditionnelles en Guyane" ("Traditional Pharmacopeias in Guiana") by Pierre GRENAND et al., published by ORSTOM, Paris 1987, pages 400–401 and 508–509, and "A Modern Herbal" by Mrs M. GRIEVE, edited by Mrs C. F. LEYEL, published by PENGUIN BOOKS, page 178).

*Simaba cedron* (Planch.), in particular, is a tree of the forests of Central America, especially Guiana. The natives use the roots of this tree as an anthelmintic or as an antimalarial remedy. They also use the bark as a decoction for the preparation of baths intended for treating skin eruptions of various origins. Finally, the seeds of this tree have long been used as a remedy for snake bites, both by local application to the wound and by ingestion.

Now, the inventors of the present invention have been able to observe that simaba extracts are particularly active on the melanocytes as regards the inhibition of melanogenesis, and it has been possible to demonstrate this activity by means of in vitro tests on melanocyte cultures, which will be described below. Furthermore, it has been possible to observe that simaba extracts are also particularly active in promoting keratinocyte differentiation and can thus be used for treating skin disorders accompanied by keratinocyte differentiation disorder. In the epidermis, this differentiation manifests itself in particular by a greater cell cohesion, by a regulation of the transformation of keratinocytes to horny cells through loss of the nucleus and increase in the cell cornification, and by an increase in the number of layers of horny cells forming the stratum corneum, these phenomena together contributing to enhancement of the protective function of the skin against the external environment and to enhancement of the water barrier, which prevents excessive water loss through the epidermis; in the hair follicle, this differentiation manifests itself by a regulation of the processes of keratin synthesis by the keratinocytes, these proteins being the principal constituent of the hair shaft, the quality of which is essential for good hair condition. Moreover, the inventors have been able to observe that these extracts make it possible to promote, accelerate and improve the differentiation of the skin cells, in particular the keratinocytes, when they are cultured in a culture medium.

One object of the present invention is thus to solve the new technical problem which consists in providing a novel formulation of cosmetic or pharmaceutical compositions, especially dermatological compositions, having a good depigmentation efficacy, thereby making it possible to use it for treating patchy skin pigmentation, in particular liver spots, and, in the treatment of vitiligo, for reducing the contrast between the zones affected by vitiligo and the surrounding zones. It will be noted in this connection that liver spots are the result of complex phenomena which generally include local hypercoloration associated with hyperpigmentation and sometimes accompanied by localized hyperkeratosis.

A further main object of the present invention is to solve the technical problem which consists in providing a novel formulation of cosmetic or pharmaceutical composition, especially dermatological composition, which has an activity promoting keratinocyte differentiation and is intended in particular for treating skin disorders accompanied by keratinocyte differentiation disorder, such as psoriasis, restoring, preserving and/or enhancing the protective function of the skin, especially the water barrier function, thereby producing a moisturizing effect, in particular by preventing excessive water loss through the epidermis, an advantageous application of which is the treatment of ichthyotic skin and the treatment of psoriatic skin, and improving the quality of the hair, thereby making its appearance more attractive.

A further main object of the present invention is to solve the new technical problem which consists in providing a solution making it possible to promote, accelerate and improve the differentiation of skin cells, especially keratinocytes, in culture.

The present invention solves these technical problems for the first time in a satisfactory manner which can be used on the industrial scale for the preparation of cosmetic or dermatological compositions or for the preparation of skin cell culture media, especially for mass culture.

Thus, according to a first feature, the present invention relates to the use of a simaba extract for the manufacture of a cosmetic or pharmaceutical composition, especially dermatological composition, which has especially a depigmentation activity and is intended in particular for treating patchy skin pigmentation, especially liver spots, treating vitiligo and skin disorders accompanied by keratinocyte differentiation disorder, such as psoriasis, restoring, preserving and/or enhancing the protective function of the skin, especially the water barrier function, and the cohesion of the epidermal cells, or else improving the quality of the hair, or for the preparation of a cell or tissue culture medium, especially for the mass culture of skin cells, in particular keratinocytes.

According to one particular characteristic, the above-mentioned extract is obtained from *Simaba cedron* (Planchon), *Simaba cuspidata* (Spruce), *Simaba moretii*, *Simaba multiflora* (Adr. Juss.) or *Simaba guyanensis* (Aublet Engl.), especially from the barks of trunks, stalks or roots of these plants.

According to another particular characteristic, the abovementioned extract is an extract obtained by extraction with at least one polar solvent such as water, an alcohol, preferably a lower alcohol such as methanol or ethanol, a glycol, in particular propylene glycol, or an aqueous-alcoholic mixture in any proportions.

According to another particular characteristic, the abovementioned extract is present in the composition at a concentration of between 0.001 and 5% by weight, preferably of between 0.01 and 1% and particularly preferably of between 0.1 and 0.5% by weight, expressed as dry extract and based on the total weight of the composition.

According to another particular characteristic, the abovementioned composition also contains an active agent selected from the group consisting of kojic acid and salts or esters thereof, caffeic acid and salts or esters thereof, hydroquinone and derivatives thereof, a mulberry extract, tretinoin, vitamin A or derivatives or esters thereof, a carotenoid, especially betacarotene, vitamin C, a corticoid, glutathion, cysteine, and parahydroxycinnamic acid or salts or esters thereof, the salts, esters and derivatives of the above-mentioned substances being selected from those which are cosmetically or pharmaceutically acceptable.

According to yet another particular characteristic, the abovementioned composition can also contain at least one moisturizer such as hyaluronic acid.

According to another particular characteristic, the abovementioned mulberry extract is present in a proportion by weight of between 0.001 and 5%, preferably of between 0.01 and 1% and particularly preferably of between 0.1 and 0.8% by weight, based on the total weight of the composition.

According to yet another particular characteristic, the abovementioned kojic acid or salts or esters thereof is present in the composition in a proportion by weight of between 0.001 and 5% and preferably of between 0.01 and 2% by weight, based on the total weight of the composition.

According to another particular characteristic, the abovementioned simaba extract is at least partially incorporated into hydrated lipidic lamellar phases or into liposomes, either by itself or in combination with at least one other active substance present in the composition.

The liposomes at least partially containing the abovementioned simaba extract can be prepared by one of the known processes for incorporating active substances into liposomes.

In one preferred embodiment according to the present invention, the process used involves atomization of the constituents of the lipidic phase, making it possible to obtain a lipidic powder which is readily dispersible in an aqueous solution to form liposomes, for example by the process described in the document U.S. Pat. No. 4,508,703. The resulting liposome suspension can be homogenized by means of ultrasound or, in the case of mass production, by means of homogenization under pressure by the process described in U.S. Pat. No. 4,621,023.

The abovementioned simaba extract can be incorporated either into the lipidic phase or into the aqueous phase of the liposomes, in particular by using the processes described above. In the case of incorporation into the lipidic phase of the liposomes, a possible procedure is as follows. The simaba extract and the constituents of the lipidic phase are dissolved, before atomization, in an organic solution containing at least one amphiphilic lipid such as soya lecithin, and optionally a lipophilic hydrophobic compound such as a sterol, in particular cholesterol or β-sitosterol. The solvent is preferably chosen from dichloromethane, chloroform, methanol or a mixture thereof.

The organic solution can advantageously contain an antioxidant such as α-tocopherol.

The lipidic powder obtained is dispersed in a suitable aqueous medium, for example a PBS solution, a glucose solution or a sodium chloride solution, to give a liposome suspension.

In one advantageous embodiment and especially in the case of a liposome composition, after the composition obtained has been homogenized, if appropriate, the liposome compositions are gelled by being mixed with a gel such as a vinylic polymer gel, in particular the one marketed under the tradename Carbopol® 940. This gelling procedure is also described in U.S. Pat. No. 4,508,703, in particular in the Examples.

In one advantageous embodiment of the invention, the concentration of the abovementioned simaba extract is between 0.001 and 30% by weight, preferably between 0.01 and 10% by weight, of the lipidic phase of said liposomes.

According to a second feature, the present invention further relates to a cosmetic or pharmaceutical composition, especially dermatological composition, preferably for topical application, which has especially a depigmentation activity as well as an activity promoting keratinocyte differentiation, and which is intended in particular for treating patchy skin pigmentation, especially liver spots, treating vitiligo and skin disorders accompanied by keratinocyte differentiation disorder, such as psoriasis, restoring, preserving and/or enhancing the protective function of the skin, especially the water barrier function, thereby making it possible especially to obtain a moisturizing effect by preventing excessive water loss through the epidermis, hence permitting use especially for the treatment of dry skin irrespective of the degree of dryness, including ichthyotic skin and psoriatic skin, and improving the quality of the hair, thus making it more attractive, characterized in that said composition comprises a cosmetically or pharmaceutically effective amount, especially a dermatologically effective amount, of a simaba extract.

Other particular characteristics of the cosmetic or pharmaceutical composition, especially dermatological composition, are clearly apparent from the foregoing description relating to the various particular characteristics of the use, and are also apparent to those skilled in the art from the complete description of the invention, which is illustrated especially by the Examples below.

An above-described composition according to the invention, containing a simaba extract, optionally in a form at least partially incorporated in hydrated lipidic lamellar phases or in liposomes, can be presented in different forms usable in cosmetics or dermatology. For example, these compositions can be gels, cremes, milks or lotions.

The effect of these compositions, when applied to the zones of the skin or scalp to be treated, is to regulate the keratinocyte differentiation, thereby promoting the formation and restoration of an epidermis of good quality, especially in the stratum corneum, enhance the barrier function of the skin which protects the epidermis, in particular the water barrier function, and make the hair more attractive, as explained above in the context of the effects and advantages of this differentiation.

Thus, in one particular embodiment, the cosmetic or dermatological composition according to the invention has a moisturizing capacity, especially by preventing excessive water loss through the epidermis, and can be intended for the treatment of dry skin, especially ichthyotic skin.

In another particular embodiment, the cosmetic or dermatological composition according to the invention makes it possible to restore normal differentiation of the keratinocytes during their transformation to horny cells, accompanied by loss of the nucleus and cell cornification. This composition can thus be intended for the treatment of psoriatic skin.

In this context, the simaba extract is usually incorporated into a cosmetically or dermatologically acceptable excipient. The simaba extract can also be incorporated into hydrated lipidic lamellar phases or into liposomes, as described for the first feature above.

According to a third feature, the present invention further relates to a cell or tissue culture medium, especially for the culture of skin cells, in particular keratinocytes, making it possible to promote, accelerate and improve their differentiation, characterized in that said culture medium comprises an effective amount of a simaba extract for obtaining said differentiation.

According to a fourth feature, the invention further relates to a process for promoting, accelerating or improving the differentiation of skin cells, in particular keratinocytes, especially in the context of a mass culture of skin cells, for the production of artificial skin or for the preparation of models of reconstituted skin, characterized in that the culture medium used is as defined in the foregoing description or in the following description taken in its entirety.

The so-called cell differentiation process according to the invention is of great interest to industry in particular. Examples which may be mentioned are:

the production of biochemical mediators by the mass culture treatment of keratinocytes in bioreactors;

the preparation of artificial skin with a view to producing skin grafts, the process of the invention being particularly advantageous in the case of autografts for major burns by virtue of the time saved in the preparation of artificial skin. In particular, the acceleration and improvement in keratinocyte differentiation manifests itself by the more rapid formation of a stratum corneum of good quality;

the production of skin models comprising reconstituted skin, intended for example for evaluating the skin penetration or the toxicity of a substance or composition applied topically, when it is intended in particular for a local treatment or especially for a systemic (transdermal) treatment.

In one particular variant, this culture process will generally comprise the preparation of a culture medium for the growth of human keratinocytes, said culture medium comprising a DMEM nutritive base medium (Gibco®), an epidermal growth factor (EGF), 10% of fetal calf serum, isoproterenol and/or forskolin, and also hydrocortisone. Within the framework of the invention, this medium also comprises a simaba extract such as described in the foregoing or following description, generally at a concentration of 0.01 to 0.5% by weight.

In this process, a mass culture of skin cells is produced by inoculating keratinocytes so as to immobilize them on supports such as hollow fibers, microbeads or microporous matrices, using the above culture medium. It is possible to ensure perfusion of the medium so as to have a sufficient supply for growth and differentiation, even when the biomass is substantial.

The culture medium according to the invention can advantageously be used for the mass culture of skin cells, in particular keratinocytes, for the production of artifical skin or for the preparation of models of reconstituted skin.

According to a fifth feature, the present invention also covers a cosmetic or dermatological method of treating skin hyperpigmentation phenomena, including particularly liver spots and other patchy skin pigmentation, characterized in that a simaba extract is applied, at least to the patchy skin pigmentation to be treated, in an effective amount for reducing it. Advantageously, this extract is obtained from the plant *Simaba cedron* (Planch.), especially from the barks. Particular extracts have been described in the foregoing description.

In another embodiment, the present invention further relates to a cosmetic or dermatological method of treating vitiligo, characterized in that a simaba extract is applied, at least to the pigmented zones of the skin adjacent to the zones depigmented by vitiligo, in an effective amount for reducing the pigmentation of said pigmented zones, thereby reducing the contrast between the pigmented zones affected by vitiligo and the surrounding zones, improving the subject's esthetic appearance.

For one or other of the foregoing features, the extract can be applied in the form of a composition containing a simaba extract at a concentration of between 0.001 and 5%, preferably of between 0.01 and 1% and particularly preferably of between 0.1 and 0.5% by weight, expressed as dry extract and based on the total weight of the composition.

In the case of use in a culture medium, in one particular variant, it is possible to use from 0.01 to 0.5% by weight of simaba extract, based on the total weight of the final culture medium.

Furthermore, in one particularly advantageous embodiment, a complementary active principle, in particular a moisturizer such as hyaluronic acid, can be introduced into the cosmetic or dermatological composition.

Also, within the framework of the invention, if the composition is a cosmetic composition, the abovementioned simaba extract can advantageously be incorporated into a cosmetically acceptable excipient.

Likewise, if this composition is a pharmaceutical composition, especially dermatological composition, the abovementioned simaba extract can be incorporated into a pharmaceutically acceptable excipient, especially a dermatologically acceptable excipient.

Such excipients are well known to those skilled in the art and also follow from the description of several Composition Examples below.

In one particular variant, the excipient of the cosmetic composition or pharmaceutical composition at least partially consists of solid particles of very small dimensions, in particular of the order of 0.05 µm to 100 µm, and the simaba extract, as the active substance, is at least partially distributed over the surface of said particles, as described in French patent application FR-A-2 685 635.

Thus other objects, characteristics and advantages of the invention will become clearly apparent from the following explanatory description referring to several illustrative Examples of the invention, which cannot therefore in any way limit the scope of the invention. In the present description, including the Examples, the percentages are given by weight unless indicated otherwise.

EXAMPLE 1 OF THE INVENTION

Aqueous extract of simaba bark

An extract of root bark of the tree *Simaba cedron* (Planch.), originating from Guiana, is subjected to a Soxhlet-type extraction with water, i.e. under reflux for several hours. The solvent/bark ratio is generally 10/1 by weight.

After extraction, this extract is generally concentrated for cosmetic or pharmaceutical use. The concentrated extract is called product I1.

Of course, as can easily be understood by those skilled in the art, the removal of the solvent, in this case water, can be continued, by evaporation under reduced pressure or by lyophilization, until a dry extract is obtained.

EXAMPLE 2 OF THE INVENTION 100 g of root bark of the tree *Simaba cedron* (Planch.), originating from Guiana, are extracted with 1 l of methanol by the Soxhlet method for several hours under reflux.

After extraction, the methanolic extract is concentrated until a product containing very little methanol, called product I2, is obtained.

EXAMPLE 3

Demonstration of the depigmentation activity of the extracts according to the invention The depigmentation activity of the extracts according to the invention is determined at different non-cytotoxic concentrations on cultures of melanocytes of the Cloudman S91 line originating from ATCC and carrying the reference CCL 53.1 clone M-3. Each extract concentration is tested on three culture dishes. The culture dishes are prepared by introducing 200.000 S91 cells per dish into a culture medium consisting of complete EMEM containing 2% v/v of fetal calf serum and 0.08 µg/ml of mitomycin C.

After 24 h of incubation at 37° C. under a moist atmosphere, the medium is replaced with an identical medium containing the test products but now not containing mitomycin C.

5 days of incubation after the replacement of the medium, the melanocytes are counted with a counting apparatus such as the Counter Coulter® and the melanin content of the cells is determined by measuring the absorbance at 405 nm and then by converting this value to the amount of melanin by means of a standard curve set up with synthetic melanin originating from SIGMA, which establishes a linear relationship between known amounts of melanin and the absorbance at 405 nm. The amount of melanin is then adjusted to correspond to $10^6$ melanocytes.

In parallel, a control culture of melanocytes was prepared in three dishes with the same cell line and under the same culture conditions except that the replacement medium introduced 24 h after incubation does not contain any test product according to the invention.

The results obtained by calculating the mean for each extract concentration over the three dishes used are listed in Tables I and II for each of the products I1 and I2 of Examples 1 and 2.

The significance of the results is determined by the statistical Student t test with a level of 0.05, which compares the product-treated cultures with the untreated control cultures.

TABLE I

| Product I1 microgram/ml | Number of cells × $10^{-3}$ | Melanin µg/$10^6$ cells | Activity A | t |
|---|---|---|---|---|
| 10 | 210 ± 20 | 23 ± 4 | +54% | S |
| 2.5 | 236 ± 10 | 36 ± 3 | +23% | S |
| 1 | 244 ± 8 | 38 ± 2 | +19% | S |
| Control | 236 ± 30 | 40.48 | 0 | |

TABLE II

| Product I2 microgram/ml | Number of cells × $10^{-3}$ | Melanin µg/$10^6$ cells | Activity A | t |
|---|---|---|---|---|
| 2.8 | 243 ± 7 | 30.6 ± 0.9 | +24.3% | S |
| Control | 236 ± 30 | 40.48 | 0 | |

S = significant

The depigmentation activity A is calculated as follows:

$$A = \frac{T-P}{T} \times 100$$

in which

T=melanin content in micrograms per $10^6$ cells of the control sample, and

P=melanin content in micrograms per $10^6$ cells of the test product I1 or I2.

Table I shows that the product I1 produces a depigmentation activity of at least 19% relative to the control, even at the very low dose of 1 µg/ml, this activity increasing to 54% for a dose of 10 µg/ml.

Again, Table II shows that the product I2 provides a depigmentation activity of at least 24.3% at the low dose of 2.8 µg/ml. Thus the products I1 and I2 have a considerable depigmentation activity.

Furthermore, the activity of the products I1 and I2 is significant as from the first test dose of 0.1 µg/ml.

EXAMPLE 4

Test for activity of Simaba cedron extract on keratinocyte differentiation

The present study is carried out using a skin sample taken from a twenty-year-old woman during a mammaplasty operation.

On day D=-2, 12 wells of a multiwell culture plate are inoculated with 300,000 cells per well of keratinocytes isolated from this sample in a conventional keratinocyte culture medium well known to those skilled in the art. Advantageously, this culture medium can be made up of an M199 medium supplemented with 2 mM L-glutamine, 10% of fetal calf serum, cholera toxin, hydrocortisone and EGF.

On days D=1, D=5, D=8 and D=11, the culture medium is replaced with an identical medium in 6 of the 12 wells, being untreated control wells; in the 6 remaining wells, being the treated wells, the culture medium is replaced with an identical medium but in which 2.5 µg/ml of *Simaba cedron* extract as obtained in Example 2, or product I2, have been dissolved; these wells are subjected to sterilizing filtration, for example on a 0.22 µm filter.

On day D=12, the cells are counted and included in epoxy resin after fixing and labeling of the cell structures with uranyl acetate.

Ultrathin sections are cut from each of the resulting resin blocks, for example using a device known as a microtome, and said section is observed under a transmission electron microscope.

The sections of the six control cultures, on the one hand, and the sections of the six cultures treated with the *Simaba cedron* extract, on the other, were then observed.

It could be seen that the cells treated with the Simaba cedron extract according to the invention, for example the extract I2 obtained in Example 2, exhibit a markedly greater cell differentiation than the control, i.e.:

from 5 to 10 cell layers, whereas the control has an average of 3 to 6 cell layers;

the upper layers of the treated cultures exhibit regular cornification with long, well-formed horny cells and little intercellular space, whereas the upper layers of the control cultures generally possess non-differentiated horny cells and a non-uniform stratification;

the desmosomes of the intermediate layers of the treated cultures are large and well differentiated, whereas the desmosomes of the control cultures are only at the stage of incipient differentiation;

also, the upper layers of the treated cultures have a very much greater keratin density than that observed in the same upper layers of the control cultures.

These distinctly superior results for the cell differentiation obtained with the *Simaba cedron* extract according to the invention makes it possible to consider the application of *Simaba cedron* extracts to the preparation of cosmetic or pharmaceutical compositions, especially dermatological compositions, and the following in particular:

compositions promoting the formation of a well-differentiated epidermis, i.e. giving a "beautiful" skin with a pleasant texture and feel;

compositions combating epidermal differentiation disorders which occur especially during ageing;

compositions enhancing the skin's barrier and hence protecting from external aggression, for example by allergens or surfactants, on the one hand, and limiting excessive water loss through the epidermis, on the other;

compositions for improving the quality of the hair, especially by improving the quality of the keratin in the hair shaft, originating from the activity of the follicular keratinocytes, which differentiate from the base of the hair.

It is also possible to consider the application of these extracts to the preparation of cell culture media, in particular those intended for the mass culture of keratinocytes, or of compositions intended for the treatment of keratinocyte cultures for favoring the rate and/or the architectural quality of these cultures, in particular when they are intended for the manufacture of artificial skin or so-called equivalent skin for grafts, in particular on burns, or else for the preparation of models intended for evaluating the toxicity or the skin penetration of various test substances.

Various Examples of cosmetic or pharmaceutical compositions according to the invention, especially dermatological compositions according to the invention, using a simaba extract, are given below.

EXAMPLE 5

Cosmetic or dermatological depigmenting composition in the form of a gel
lyophilized aqueous extract of Simaba cedron bark of Example 1 . . . 0.3 g
propylene glycol . . . 4 g
ethanol . . . 3 g
2% Carbopol 940® gel+preservative.qsp 100 g This gel is applied locally twice a day for 6 weeks to the zones of skin to be depigmented.

EXAMPLE 6

Cosmetic or dermatological composition containing a simaba extract in liposomes, in the form of a gel 0.3 g of the product I2 of Example 2 is dissolved in 50 ml of an 8/2 (v/v) dichloromethane/methanol mixture, to which 9 g of soya lecithin and 1 g of cholesterol are added.

The solution obtained can be treated to give a liposome suspension by the well-known rotary evaporation method, which consists in depositing a lipidic layer in the round-bottomed flask of the rotary evaporator by evaporation of the solvent, and then adding water or an appropriate aqueous solution containing preservatives well known to those skilled in the art, to give 100 g of aqueous liposome suspension.

This suspension can be homogenized by means of ultrasound at a power of 150 W for 10 min at 4° C.

The homogenized liposome suspension obtained is then gelled by the addition of an equivalent weight of 2% Carbopol 940® gel neutralized with triethanolamine.

This gives a gelled composition containing 0.15% by weight of the product I2, at least partially incorporated in the lipidic bilayer of the liposomes, based on the total weight of the composition.

This composition can be applied locally, for example once a day for 4 weeks, in order to reduce liver spots.

EXAMPLE 7

Depigmenting gel
aqueous extract of *Simaba cedron* (Planch.) root bark according to Example 1 . . . 0.2
mulberry extract . . . 0.35
ascorbic acid . . . 0.6
Carbopol 940® . . . 2.0
water+preservatives . . . qsp 100 g This gel is applied locally to the patches.

EXAMPLE 8

Bleaching creme for lightening the skin
methanolic extract of Simaba cedron (Planch.) root bark according to Example 2 . . . 0.3
Héliocarotte® . . . 1.5
mineral oil . . . 4.0
kojic acid . . . 0.5
glyceryl stearate . . . 4.0
PEG 30 glyceryl stearate . . . 3
water+preservative . . . qsp 100 g HELIOCAROTTE® takes the form of an oil containing 0.05% of β-carotene. It is commercially available from BERTIN, Courbevoie—France.

This creme is applied locally twice a day in four-week courses of treatment.

EXAMPLE 9

Dermatological depigmenting gel
ethanolic extract of Simaba cedron (Planch.) root bark . . . 0.45
retinoic acid . . . 0.02
alcohol . . . 30.0
Carbopol 940® . . . 2.5
water+preservative and antioxidant . . . qsp 100 g The abovementioned ethanolic extracts were obtained by the process described in Example 2 except that the methanol was replaced with ethanol.

This gel is applied to the dark zones twice a day for three weeks.

EXAMPLE 10

Milk for lightening the skin
aqueous extract of *Simaba guyanensis* (Aubl. Engl.) root bark prepared by the extraction method described in Example 1 . . . 1.5 hydroquinone ... 1.5
Héliocarotte® ... 2
wheatgerm oil ... 3
tocopherol linoleate ... 0.5
glycerol ... 2
Carbopol ... 0.5
glyceryl stearate ... 2.0
PEG 30 glyceryl stearate ... 3.0
perfumes+solubilizer ... 0.15
water+preservative ... qsp 100 g This milk is applied to the parts of the body to be treated, after a shower, once a day in two- to three-week courses of treatment.

This creme is applied locally twice a day in four-week courses of treatment.

EXAMPLE 11

Dermatological composition for restoring the epidermal water barrier aqueous extract of *Simaba cedron* (Planch.) root bark of Example 1 ... 0.5 g
Cremophor RH 40® ... 1 g
Carbomer 980® ... 0.2 g
triethanolamine ... 0.18 g
PEG 6-30 of stearate ... 7 g
cetyl alcohol ... 2 g
vegetable oils ... 25 g
perfumed aqueous excipient ... qsp 100 g The components are mixed in conventional manner to give a treating emulsion, which is applied morning and evening by gently massaging the zones to be treated. This emulsion is used as a day and/or night creme.

EXAMPLE 12

Dermatological composition for the treatment of psoriatic skin methanolic *Simaba cedron* extract of Example 2 ... 0.3 g
2% Carbopol 980® gel ... 35 g
perfumed aqueous excipient ... qsp 100 g The *Simaba cedron* extract is introduced into the aqueous excipient in order to disperse it, after which the Carbopol gel is added to give a gelled composition, which is applied locally to the lesions for 6 weeks.

EXAMPLE 13

Cosmetic composition for maintaining a satisfactory state of hydration of the epidermis methanolic *Simaba cedron* extract of Example 2 ... 0.18 g
α-bisabolol ... 0.1 g
hyaluronic acid ... 1 g
urea ... 3 g
cosmetically acceptable excipient in the form of a body milk ... qsp 100 g The milk is applied to the zones to be treated, in particular to the legs after depilation. This composition makes it possible in particular to enhance the water barrier function of the epidermis by improving the epidermal intercellular cohesion. It thus enables the skin to preserve a satisfactory state of hydration.

EXAMPLE 14

Liposomal cosmetic composition for rebalancing the desquamation of the stratum corneum of the epidermis and restoring a smooth epidermis methanolic *Simaba cedron* extract of Example 2 ... 0.1 g
soya lecithin ... 2 g
β-sitosterol ... 0.2 g
squalane-based cosmetic creme emulsion of the oil-in-water type ... qsp 100 g The first step is to prepare an aqueous liposome suspension encapsulating the methanolic *Simaba cedron* extract of Example 2 in the lipidic phase of said liposomes. This is done by the following procedure.

0.1 g of the methanolic Simaba cedron extract of Example 2, 2 g of soya lecithin and 0.2 g of β-sitosterol are dissolved in 50 ml of a 4:1 mixture of dichloromethane and methanol. This solution is evaporated under reduced pressure (about 200 mm of mercury) in a rotating round-bottomed flask heated to 45° C. The lipidic film obtained is taken up with 25 ml of an aqueous solution containing 0.2 g/l of monopotassium phosphate and 1.44 g/l of disodium phosphate, with shaking for 1 h.

This gives about 25 ml of a liposome suspension encapsulating the *Simaba cedron* extract, which is then homogenized with ultrasound (15 min, 150 W, 4° C.).

The second step is to incorporate the resulting liposome suspension into the emulsified excipient, in conventional manner, to give the creme according to the invention.

The creme can be applied daily to the face in cases of rough skin which desquamates in scales.

This composition enhances the cohesion of the stratum corneum and normalizes the detachment of the dead cells.

EXAMPLE 15

Cosmetic composition containing a *Simaba cedron* extract, intended for the preventive treatment of dry skin methanolic *Simaba cedron* extract obtained in Example 2 ... 0.5 g
creme emulsion excipient of the oil-in-water type ... qsp 100 g The methanolic Simaba cedron extract of Example 2 is incorporated into the creme emulsion excipient, in conventional manner, to give the creme according to the invention.

The creme can be applied daily to the parts of the body which it is desired to treat.

EXAMPLE 16

Cosmetic composition containing a simaba extract, intended for the treatment of ichthyotic skin glycerol ... 3 g
hyaluronic acid ... 1 g
aqueous *Simaba cedron* extract of Example 1 0.2g
creme emulsion excipient of the oil-in-water type ... qsp 100 g The aqueous *Simaba cedron* extract obtained in Example 1, the glycerol and the hyaluronic acid are incorporated into the creme emulsion excipient, in conventional manner, to give the creme according to the invention.

This creme is applied daily to the desired zones of the skin until a much smoother skin is obtained by virtue of regular renewal of the stratum corneum.

EXAMPLE 17

Preparation of a culture medium and its use for the mass culture of skin cells

For the preparation of this culture medium and its use for the mass culture of skin cells, those skilled in the art may refer especially to the article by Philip C. Familletti et al. in Biotechnology, vol. 6, January 1988, pages 41 to 44, and to the references cited in said article, in particular Arathoon et al. in Science (1986), 232, page 1390 et seq., and the article by Ku K. et al. in Biotechnology, Bioeng. (1980), 23, pages 79 et seq.

Thus an optimal culture medium for the growth of human keratinocytes is prepared which comprises a DMEM nutritive base medium (Gibco®), EGF, 10% of fetal calf serum, isoproterenol and/or forskolin, and hydrocortisone.

This medium will include a simaba extract according to the invention, preferably at a concentration of 0.01 to 0.5% by weight of simaba extract, based on the total weight of the final culture medium.

A culture based on skin cells is produced by inoculating keratinocytes so as to immobilize them on supports such as hollow fibers, microbeads or microporous matrices, using the culture medium described above. Perfusion of the medium, in a perfusion system of the type described by Sylvie GUICHARD-BALESTRINI in Biofutur, supplement no. 56, April 1987, pages 2 to 14, will be ensured so as to have a sufficient supply for growth and differentiation, even when the biomass is substantial.

When culture has ended, the substance secreted by the keratinocytes are recovered; they mainly contain lipids, which are sources of starting material for the formulation of cosmetic or pharmaceutical compositions for topical application to the epidermis or scalp.

The product of the invention makes it possible to treat reconstituted skin cultures, in particular cultures of keratinocytes or other epidermal cells cultivated on an appropriate support such as a collagen support (optionally containing fibroblasts), for example the one described in the document La Recherche (1987), no. 185, pages 149–159, and in Br. J. Dermatol. (1986), 114, pages 91–101, or a support consisting of excised dermis.

A more rapid and more complete epidermization will be obtained by using the composition according to the invention. This will make it possible to provide doctors more rapidly with reconstituted skin, which is a kind of biological dressing for autografts, for example in the case of extensive burns. The invention will also enable reconstituted skin of good quality to be produced industrially and competitively for carrying out penetration or tolerance tests.

The invention of course includes all the constituent means of technical equivalents of the means described, as well as various combinations thereof.

The invention also covers any characteristic which appears to be novel relative to any state of the art, based on the present description taken in its entirety.

We claim:

1. A method of treatment of body areas in need of treatment selected from the group consisting of depigmentation, promoting keratinocyte differentiation, preserving or enhancing protective function of skin, improving cohesion of epidermal cells and improving the quality of hair, comprising delivering to said body areas an amount of a simaba extract effective for performing said treatment.

2. The method of claim 1 wherein said treatment is preserving or enhancing protective function of skin, and wherein said treatment is in enhancing the water barrier function.

3. The method of claim 1 wherein said treatment is depigmentation, and wherein said treatment is selected from the group consisting of treatment of patchy skin pigmentation, treatment of liver spots, treatment of vitiligo, treatment of skin disorders accompanied by keratinocyte differentiation disorder, treatment of psoriasis, treatment of ichthyotic skin, and a treatment of dry skin.

4. The method of claim 1 wherein said simaba extract is an extract obtained by extraction with at least one polar solvent.

5. The method of claim 4 wherein said polar solvent is selected from the group consisting of water, an alcohol, a glycol, or an aqueous-alcoholic mixture.

6. The method of claim 5 wherein the alcohol is a lower alcohol.

7. The method of claim 6 wherein the lower alcohol is selected from the group consisting of methanol and ethanol.

8. The method of claim 1 wherein the simaba extract is obtained from a plant selected from the group consisting of *Simaba cedron* (Planchon), *Simaba cuspidata* (Spruce), *Simaba moretii*, *Simaba multiflora* (Adr. Juss.) and *Simaba guyanensis* (Aublet Engl.).

9. The method of claim 8 wherein the simaba extract is obtained from the barks, trunks, stalks or roots of the plant.

10. The method of claim 1 wherein the simaba extract delivered to said body areas is in the form of a composition comprising the simaba extract in a cosmetically or pharmaceutically topically acceptable excipient, and wherein the simaba extract is present in the composition at a concentration of between 0.001 and 5% by weight.

11. The method of claim 10 wherein the simaba extract is present in the composition at a concentration of between 0.01 and 5% by weight.

12. The method of claim 10 wherein the simaba extract is present in the composition at a concentration of between 0.01 and 1% by weight.

13. A cosmetic or pharmaceutical composition for topical application comprising a cosmetically or pharmaceutically topically effective amount of a simaba extract in a cosmetically or pharmaceutically topically acceptable excipient.

14. The cosmetic or pharmaceutical composition of claim 13 wherein the simaba extract is incorporated in hydrated lipidic lamellar phases or into liposomes.

15. The cosmetic or pharmaceutical composition of claim 14 wherein the concentration of the extract is between 0.001 and 30% by weight of the lipidic phase of the liposomes.

16. The cosmetic or pharmaceutical composition of claim 13 wherein the simaba extract is present in the composition at a concentration of between 0.001 and 5% by weight.

17. The cosmetic or pharmaceutical composition of claim 13 wherein the simaba extract is present in the composition at a concentration of between 0.01 and 5% by weight.

18. The cosmetic or pharmaceutical composition of claim 13 wherein the simaba extract is present in the composition at a concentration of between 0.01 and 1% by weight.

19. A method of promoting, accelerating or improving the differentiation of skin cells, comprising perfusing a culture of said skin cells in a culture medium comprising an effective amount of a simaba extract for obtaining said differentiation.

20. The method of claim 19 wherein the culture medium comprises from 0.001 to 5% by weight of simaba extract.

21. The method of claim 19 wherein the culture medium comprises from 0.01 to 0.5% by weight of simaba extract.

22. The method of claim 19 wherein the skin cells are keratinocyte skin cells.

23. The method of claim 22 wherein the keratinocyte skin cells are human keratinocytes.

24. A culture medium for the culture of skin cells comprising an effective amount of a simaba extract for obtaining differentiation of said skin cells.

25. The culture medium of claim 24 wherein said culture medium comprises from 0.001 to 5% by weight of simaba plant extract.

26. The culture medium of claim 24 wherein said culture medium comprises from 0.01 to 0.5% by weight of simaba plant extract.

27. The culture medium of claim 24 wherein said skin cells are keratinocyte skin cells.

28. The culture medium of claim 27 wherein said keratinocyte skin cells are human keratinocytes.

29. A method of producing artificial skin comprising preparing a culture medium for the growth of human keratinocytes which comprises an amount of a simaba extract effective for producing artificial skin from said keratinocytes.

30. The method of claim 29 wherein said culture medium comprises from 0.001 to 5% by weight of a simaba extract.

31. The method of claim 29 wherein said culture medium comprises from 0.01 to 0.5% by weight of a simaba extract.

* * * * *

UNITED STATES PATENT AND TRADEMARK OFFICE
CERTIFICATE OF CORRECTION

PATENT NO.   : 5,676,949
DATED        : October 14, 1997
INVENTOR(S)  : BONTE et al.

It is certified that error appears in the above-indentified patent and that said Letters Patent is hereby corrected as shown below:

Title page,

[*]  Notice:  The term of this patent shall not extend beyond the expiration date of Pat. No. 5,676,948.

Signed and Sealed this

Tenth Day of February, 1998

Attest:

BRUCE LEHMAN

Attesting Officer

Commissioner of Patents and Trademarks